July 14, 1959 E. S. BOERNER Plant Pat. 1,850
ROSE PLANT
Filed Nov. 12, 1958
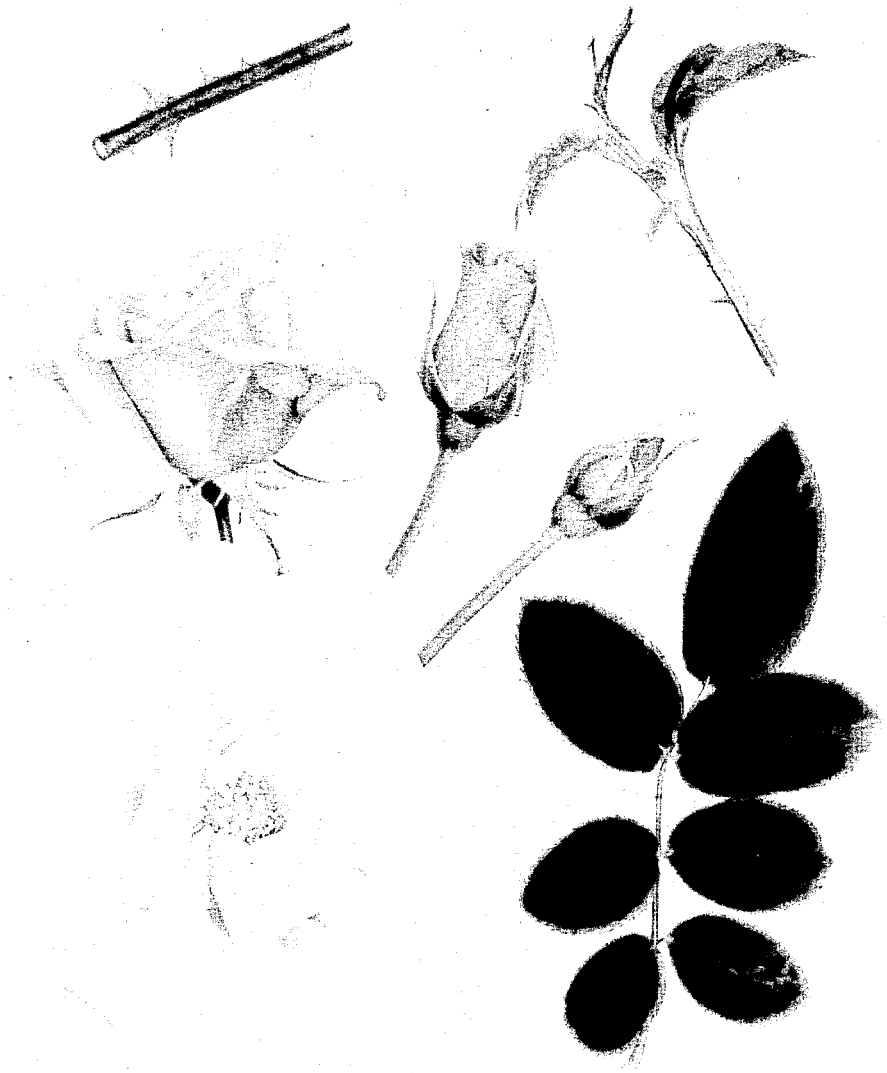
Inventor.
E. S. Boerner
By: Robb & Robb
Attorneys United States Patent Office Plant Pat. 1,850
Patented July 14, 1959

1,850

ROSE PLANT

Eugene S. Boerner, Newark, N.Y., assignor to Jackson & Perkins Company, Newark, N.Y., a corporation of New York Application November 12, 1958, Serial No. 773,530

1 Claim. (Cl. 47—61)

The present invention relates to a new and distinct variety of rose plant of the hybrid tea class, which was originated by me by crossing the variety "Enchantment" (Plant Patent No. 737) with an unnamed and unpatented floribunda seedling of "Independence" (Plant Patent No. 1,036).

The primary objective of this breeding was to produce a new rose variety which bears flowers more prolifically and of a deeper color than the variety "Enchantment." This objective was fully achieved, along with other desirable improvements, as evidenced by the following unique combination of characteristics which are outstanding in the new variety and distinguish it from its parents, as well as from all other varieties of which I am aware:

(1) Heavy dark green foliage;
(2) Many thorns distributed on the stem;
(3) Prolific flower production;
(4) Very large flowers of hybrid tea form; and
(5) A variation in the general color tonality of the flowers from Spectrum Red in the bud stage, through Rose Red, lightly overcast with Spinel Pink in the half-open bud stage, to Thulite Pink, lightly overcast with Cameo Pink in the fully open flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Enchantment."
*Pollen parent.*—An unnamed seedling of "Independence."
Classification:
*Botanic.*—Hybrid tea.
*Commercial.*—Hybrid tea.

*Flower*

(Observations made from specimens grown in a greenhouse at Newark, New York in the early afternoon in the early part of July.)

Blooming habit: Recurrent—continuous.
Bud:
*Size.*—Large.
*Form.*—Ovoid; is not affected by wet or hot weather.
*Color.*—When sepals first divide—Carmine, Plate 1. When petals begin to unfurl—Spectrum Red, Plate 1. When half-blown: inside of petals—Rose Red, Plate 12, lightly overcast with Spinel Pink, Plate 26; reverse of petals—Rose Red, Plate 12.
*Sepals.*—Branched; curl back when petals begin to unfurl. Color: inside—Kildare Green, Plate 31; outside—Light Bice Green, Plate 17.
*Calyx.* — Color — Light Bice Green, Plate 17. Shape—pear. Size—Small. Aspect—smooth. Odor when rubbed—none.
*Peduncle.*—Length — medium. Aspect — smooth. Strength—erect; slender. Color—Biscay Green, Plate 17.
*Opening.*—Opens up well; is not affected by adverse weather conditions.

Bloom:
*Size.*—Large. Average size when fully expanded—5 inches.
*Borne.*—Singly.
*Stems.*—Medium length; strong.
*Form (when first open).*—Cupped. Permanence—retains its form to the end.
*Petalage.*—Double (full but open center). Number of petals under normal conditions—from 35 to 40.
*Color.*—Center of flower—Spinel Pink, Plate 26, lightly overcast with Thulite Pink, Plate 26. Outer petals—Spinel Pink, Plate 26, lightly overcast with Deep Rose Pink, Plate 12. Base of petals (aiglet)—Primrose Yellow, Plate 30. Inside of petals—Thulite Pink, Plate 26, lightly overcast with Cameo Pink, Plate 26. Reverse of petals—Spinel Pink, Plate 26, lightly overcast with Deep Rose Pink, Plate 12. General tonality from a distance—Thulite Pink, Plate 26, lightly overcast with Spinel Pink, Plate 26.
*Discoloration.*—General tonality at end of first day—Spinel Pink, Plate 26, lightly overcast with Thulite Pink, Plate 26. Second day—Spinel Pink, Plate 26, overcast with Thulite Pink, Plate 26. Third day—Thulite Pink, Plate 26, lightly overcast with Cameo Pink, Plate 26.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Strong. Nature—"Old Rose perfume" (centifolia).
*Lasting quality.*—On the plant—long. As cut flower—long.

*Genital organs*

Stamens, anthers: Medium size; many; regularly arranged around styles. Color—Mikado Orange, Plate 3.
Stamens, filaments (threads). Medium length. Color—Eosine Pink, Plate 1.
Pollen: Color—Capucine-Buff, Plate 3.
Styles: Bunched; uneven length; medium length; thin.
Stigmas: Color—Light Buff, Plate 15.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Abundant.
*Color.*—New foliage: upper side—Oil Green, Plate 5, with edges Indian Lake, Plate 26; under side—center of leaf Lettuce Green, Plate 5, with edges overcast with Amaranth Purple, Plate 12. Old foliage: upper side—Dark Cress Green, Plate 31, under side—Bice Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Biscay Green, Plate 17. Under side—prickly.

*Stipules.*—Long; bearded.

Wood:

*New wood.*—Color—Apple Green, Plate 17. Bark—smooth.

*Old wood.*—Color—Forest Green, Plate 17. Bark—smooth.

Thorns:

*Thorns.*—Quantity: on main stalks from base—many; on laterals from stalk—many. Form— narrow base; medium length; straight. Color (when young)—Lumiere Green, Plate 17. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of heavy, dark green foliage, many thorns distributed on the stem, prolific flower production, very large flowers of hybrid tea form, and a distinctive color tonality of the flowers varying from Spectrum Red in the bud stage, through Rose Red, lightly overcast with Spinel Pink in the half-open bud stage, to Thulite Pink, lightly overcast with Cameo Pink in the fully open flowers.

No references cited.